(12) United States Patent
Grabert et al.

(10) Patent No.: US 10,274,418 B2
(45) Date of Patent: Apr. 30, 2019

(54) CALIBRATION SUSPENSION UNIT, METHOD FOR THE MANUFACTURE OF A CALIBRATION SUSPENSION UNIT AND USE OF A CALIBRATION SUSPENSION UNIT

(71) Applicant: Tintometer GmbH, Dortmund (DE)

(72) Inventors: Elmar Grabert, Herne (DE); Ulrich Lundgreen, Guetersloh (DE)

(73) Assignee: Tintometer GmbH, Dortmund (DE)

(*) Notice: Subject to any disclaimer, the term of this patent is extended or adjusted under 35 U.S.C. 154(b) by 89 days.

(21) Appl. No.: 15/454,666

(22) Filed: Mar. 9, 2017

(65) Prior Publication Data

US 2017/0268986 A1 Sep. 21, 2017

(30) Foreign Application Priority Data

Mar. 21, 2016 (EP) ..................... 16161317

(51) Int. Cl.
| | |
|---|---|
| *G01N 21/03* | (2006.01) |
| *G01N 21/11* | (2006.01) |
| *G01N 15/06* | (2006.01) |
| *G01N 21/27* | (2006.01) |
| *G01N 21/47* | (2006.01) |
| *A61J 1/10* | (2006.01) |

(Continued)

(52) U.S. Cl.
CPC ............ *G01N 21/03* (2013.01); *G01N 15/06* (2013.01); *G01N 21/11* (2013.01); *G01N 21/278* (2013.01); *G01N 21/4785* (2013.01); *A61J 1/10* (2013.01); *B01L 3/505* (2013.01); *G01N 2001/2893* (2013.01); *G01N 2015/0693* (2013.01); *G01N 2021/0364* (2013.01); *G01N 2201/13* (2013.01)

(58) Field of Classification Search
CPC ........ G01N 2021/0364; G01N 15/0806; B01L 3/505
See application file for complete search history.

(56) References Cited

U.S. PATENT DOCUMENTS

| | | | |
|---|---|---|---|
| 4,116,336 A | 9/1978 | Sorensen et al. | |
| 5,710,371 A | * 1/1998 | Czernecki | .......... G01N 27/4163 204/421 |
| 5,777,011 A | 7/1998 | Sadar | |

(Continued)

FOREIGN PATENT DOCUMENTS

| | | |
|---|---|---|
| EP | 0380949 A2 | 8/1990 |
| EP | 0724152 A2 | 7/1996 |

(Continued)

OTHER PUBLICATIONS

European Search Report dated Sep. 30, 2016 from corresponding EP Application No. 16161317.9, 11 pages.

(Continued)

*Primary Examiner* — Tri T Ton
*Assistant Examiner* — Rebecca C Bryant
(74) *Attorney, Agent, or Firm* — Dilworth IP, LLC

(57) ABSTRACT

A calibration suspension unit has a container made of a flexible material that is filled with a calibration suspension for the calibration of a turbidity meter. There exists no air supernatant above the calibration suspension in the container. Further, a method for the manufacture of a calibration suspension unit is provided and its use for the calibration of a turbidity meter is described.

18 Claims, 8 Drawing Sheets

(51) Int. Cl.
   *B01L 3/00* (2006.01)
   *G01N 1/28* (2006.01)

(56) References Cited

U.S. PATENT DOCUMENTS 6,405,872 B1 * 6/2002 Ruther .................. B01L 3/505
                                                  206/484.2
2015/0079685 A1   3/2015 Pfeiffer et al.

FOREIGN PATENT DOCUMENTS

| EP | 2077452 A1 | 7/2009 |
| WO | 00/05139 A2 | 2/2000 |
| WO | 2006034729 A1 | 4/2006 |

OTHER PUBLICATIONS

English summary of EP Search Report dated Sep. 30, 2016.
Canty, G. A. et al, Injection of Fluidized Bed Combustion Ash into Mine Workings for Treatment of Acid Mine Drainage, IMWA Springer-Verlag 2006, p. 45-55.
Sadar, Mike, Turbidity Standards, Technical Information Series, Booklet No. 12, p. 1-18.
LaMotte Company, LaMotte TC-3000 Tri-Meters manual, p. 1-78.
In-Situ Inc., Multi-Parameter TROLL 9000 WQP-100 Operator's Manual, p. 1-164.

* cited by examiner

CALIBRATION SUSPENSION UNIT, METHOD FOR THE MANUFACTURE OF A CALIBRATION SUSPENSION UNIT AND USE OF A CALIBRATION SUSPENSION UNIT

FIELD OF THE INVENTION

The invention relates to a calibration suspension unit comprising a calibration suspension for the calibration of a turbidity meter, preferably of an on-line turbidity meter, a method for the manufacture of a calibration suspension unit, and the use of a calibration suspension unit.

BACKGROUND OF THE INVENTION

Turbidity meters have to be calibrated regularly. To this end, calibration suspensions containing a turbidity calibration standard in a pre-determined concentration are often used. The calibration suspensions are made by the manufacturers themselves or obtained commercially as a finished standard suspension in canisters of various volumes. For calibration, the standard suspension is optionally diluted and introduced into the turbidity meter. Subsequently, light intensity is measured and correlated with the concentration of the turbidity calibration standard in the standard suspension.

The calibration suspensions usually comprise colloidal particles in a suitable liquid. The internationally recognized turbidity calibration standard is formazine. The manufacture of this calibration standard is described in the ISO 7027 standard.

Over time, the colloidal particles settle on the ground of the storage container. To calibrate a turbidity meter, the calibration suspensions have thus to be mixed before use. This is done by shaking or stirring of the calibration suspension in the storage container.

SUMMARY OF THE INVENTION

In a first aspect the invention provides a calibration suspension unit and a method for its manufacture which can facilitate the manageability of turbidity measurements and improve the quality of the measured values.

The inventors found out that two factors are essential for the quality of calibration of a turbidity meter with a calibration suspension:
  i) homogeneously mixing of the calibration suspension introduced into the turbidity meter, and
  ii) measuring of the calibration suspension without any additional interfering influences.

As a substantial interfering influence during the measurement of the calibration suspension air bubbles of any size present in the calibration suspensions were identified, with the smallest air bubbles being the strongest and most persisting interfering influence. However, air bubbles will almost inevitably be introduced into the calibration suspension during the required mixing, for example by shaking or stirring. On the other hand, a long wait to let in particular the very small air bubbles escape can make the colloidal particles settle again and thus lead to an inaccurate calibration.

In addition, further air bubbles can enter when the measuring chamber of the turbidity meter is filled with the calibration suspension. The air bubbles entered this way also result in a disturbance of the measurement making another wait necessary. However, this holds the danger of the colloidal particles settling in the turbidity meter thus distorting the measurement.

To solve the above mentioned problem, the invention provides a calibration suspension unit comprising a container that is filled with a calibration suspension to calibrate a turbidity meter, wherein the container is made of a flexible material, and wherein no air supernatant is present above the calibration suspension in the container.

According to the present invention a flexible material is a material that can be easily deformed by a person without using any additional tool, in particular by kneading by hand, and without damaging the container. As compared to a calibration suspension provided in a rigid container the advantage of the calibration suspension unit according to the present invention is that the calibration suspension contained in the flexible container does not include any air bubbles or air supernatant, and can already be mixed by deforming the container made of the flexible material. Unlike, for example, by shaking or stirring the suspension in a rigid canister or an open vessel, the formation of air bubbles can here be prevented to achieve an easier and safer manageability as well as a higher quality of the turbidity measurement.

According to an advantageous embodiment the container is designed as a foil bag, preferably a tubular bag. Such foil bags, as they are, for example, known in the form of infusions bags in medical technology or drink pouches in the beverages industry, can be produced in a variety of shapes and sizes at low costs.

According to another advantageous embodiment the container has a wall strength of less than 1 mm, preferably less than 0.8 mm, particularly preferably from 0.1 mm to 0.8 mm. In this embodiment it is especially easy to mechanically deform, in particular knead, the container.

The container is preferably gas-tight and impermeable to liquids. Thus, it is ensured that the calibration suspension cannot be contaminated by agents coming from outside of the container.

The container may be impermeable to light, in particular impermeable to UV light and/or visible light, to reduce undesired reactions of the turbidity standard by exposure to electromagnetic radiation.

In a preferred embodiment the container is made of a plastic film and/or a metal foil. These materials have the advantage that they are inexpensive and can be easily made into the containers having the desired properties such as flexibility. The container can also be made of a multi-layer composite film, for example of several plastic films and optionally an external metal foil or metal coating, for example made of aluminum, to combine the different properties of various films/foils.

Examples of suitable plastic films are films made of polyethylene, polypropylene, polyamide, polyurethane, polycarbonate, and (poly)ethylene vinyl acetate, as well as copolymers and composite materials thereof.

In another preferred embodiment the maximum volume of the container is larger than the volume of the calibration suspension. Therefore, the container is not plumped up, i.e. filled up to its maximum volume, with the calibration suspension, so the container can be well deformed and the calibration suspension thus be mixed homogeneously. In addition, the larger volume of the container makes sure that the compressive forces occurring in the interior of the container during kneading of the calibration suspension unit remain small thus avoiding any damage, in particular any bursting of the container.

The ratio of the volume of the calibration suspension to the maximum volume of the container is preferably from 0.2 to 0.8, preferably from 0.4 to 0.6. These filling ratios are a good compromise between material costs and deformability of the container.

According to the present invention, the calibration suspension unit is substantially free of air or gas, i.e. the calibration suspension in the flexible container does not exhibit any air supernatant and there is no dead volume in the interior of the container. For this reason, the container is only filled with the air bubble-free calibration suspension. Thus, it is ensured that the calibration suspension does not get into contact with air and no air bubbles may form in the calibration suspension either, even when the calibration suspension in the container is mixed homogeneously.

Preferably, the calibration suspension is a suspension of a calibration standard selected from at least one of formazine, styrene divinyl benzene, latex or metal oxide gel in a suitable liquid, preferably a formazine suspension.

In an advantageous embodiment the calibration suspension unit comprises a hose line system suitable for the air-free transport of the calibration suspension into a turbidity meter. The hose line system guarantees that no air bubbles enter the calibration suspension and/or form in the calibration suspension when the calibration suspension is passed from the calibration suspension unit into the turbidity meter.

The hose line system may comprise a hose line directly connected to the flexible container to create a flow connection between the flexible container and at least part of the hose line. For example, a hose line may be provided that is rigidly linked with the flexible container of the calibration suspension unit or detachably connected to the flexible container. For example, the rigid connection can be formed by the hose line being welded to the flexible container or being integral with it. Alternatively, the hose line system may be attached to the flexible container by a lid, with the hose line system forming a rigid and liquid-impermeable connection with the lid and, together with the lid, being placed on, preferably screwed on, an opening in the flexible container.

The calibration suspension unit comprising the hose line system directly connected to the flexible container is preferably tightly closed by a clamp without any air supernatant being present. To this end, the clamp at the hose line can be preferably positioned close to the flexible container and disconnect the hose line without any air bubbles being formed. As a result, the calibration suspension cannot flow from the flexible container and/or the hose line. In addition, a closure can be provided at the free end, i.e. at the end opposite to the flexible container, of the hose line to prevent a contamination of the hose line. For example, this closure may be a stopper, a welding seam or a self-locking stop valve.

In another embodiment the calibration suspension unit can comprise a separately provided hose line system. Such separate hose line systems are known, for example, from infusion bags in medical technology and, apart from the hose line for transporting the calibration suspension, usually have a device for tapping the flexible container.

The separate hose line system preferably comprises a hose line and a cannula connected to the hose line. The cannula can be used to tap the calibration suspension in the flexible container and transport it via the hose line to a turbidity meter without any air bubbles being formed.

The internal diameter of the hose line of the hose line system and optionally the cannula is preferably 9 mm at the most, preferably from 3 to 7 mm. The preferred internal diameters of the hose line and optionally the cannula have the advantage that the calibration suspension completely fills the hose line and/or the cannula and, while being transported to the turbidity meter, pushes forward the enclosed air in the hose line and/or the cannula without the calibration suspension being mixed with air. The formation of air bubbles in the calibration suspension is thus inhibited.

According to another preferred embodiment the container has an opening that is closed by a septum lid, in particular a septum lid made of plastic. According to the present invention, a septum lid is a lid with a section exhibiting self-sealing properties and intended to be punctured by a cannula. In particular, this section has a membrane or a sealing element acting as a sealing reception for a penetrating cannula.

In addition, the lid can have, at its inner surface, a process that protrudes into the opening of the container and is closed at its free end. When placing the lid on a container filled to the brim this process displaces the liquid and air that might still be present from the closure area making sure that no air is trapped in the container when closing it.

The septum lid and the opening in the container are preferably designed as a screw cap. Alternatively, the opening can also be designed as a sleeve directly formed to the container, on which the septum lid is clamped.

The turbidity meter is preferably an on-line turbidity meter. During on-line measurement, usually a sample of the process to be monitored is taken and introduced into the meter.

Another aspect of the invention is a method for the manufacture of a calibration suspension unit for the calibration of a turbidity meter comprising the following steps:
a) filling the flexible container with the calibration suspension,
b) removing substantially all air from the container, and
c) closing the container,
with no air supernatant being present above the calibration suspension in the closed container.

According to an advantageous embodiment air is removed by mechanically compressing the container. Mechanical compression can be performed, for example, by compressing the flexible container filled with the calibration suspension between two surfaces or by means of two rolls squeezing the container, and is an inexpensive method for the removal of residual air still present from the container.

According to the present invention, the calibration suspension unit described above is used to calibrate a turbidity meter, in particular an on-line turbidity meter.

According to a preferred embodiment the calibration suspension is introduced into the turbidity meter being substantially free of air bubbles. This allows the measurement to be quickly performed and ensures a particularly high quality of the measured results.

According to another preferred embodiment the calibration suspension is homogeneously mixed in a closed container by mechanically deforming the calibration suspension unit. Mechanical deformation may be performed in particular by manually compressing or kneading the calibration suspension unit, which has the advantage that air bubble formation in the calibration suspension is prevented.

In an advantageous embodiment the homogeneously mixed calibration suspension is introduced into the turbidity meter via the hose line. The calibration suspension pushes forward the air enclosed in the hose line without the calibration suspension being mixed with the air and subsequently displaces the air present in the measuring chamber of the turbidity meter to make sure that the calibration suspension is introduced into the turbidity meter without any air bubbles being formed.

As the calibration suspension escapes, the flexible container contracts without air being drawn in as a volume compensation by the calibration suspension. The air bubble-free transport of the calibration suspension into the turbidity meter is thus ensured.

BRIEF DESCRIPTION OF THE DRAWINGS

Further advantages and disadvantages result from the below description of preferred embodiments in conjunction with the attached drawings, wherein.

DETAILED DESCRIPTION OF PREFERRED EMBODIMENTS

Figure 1:
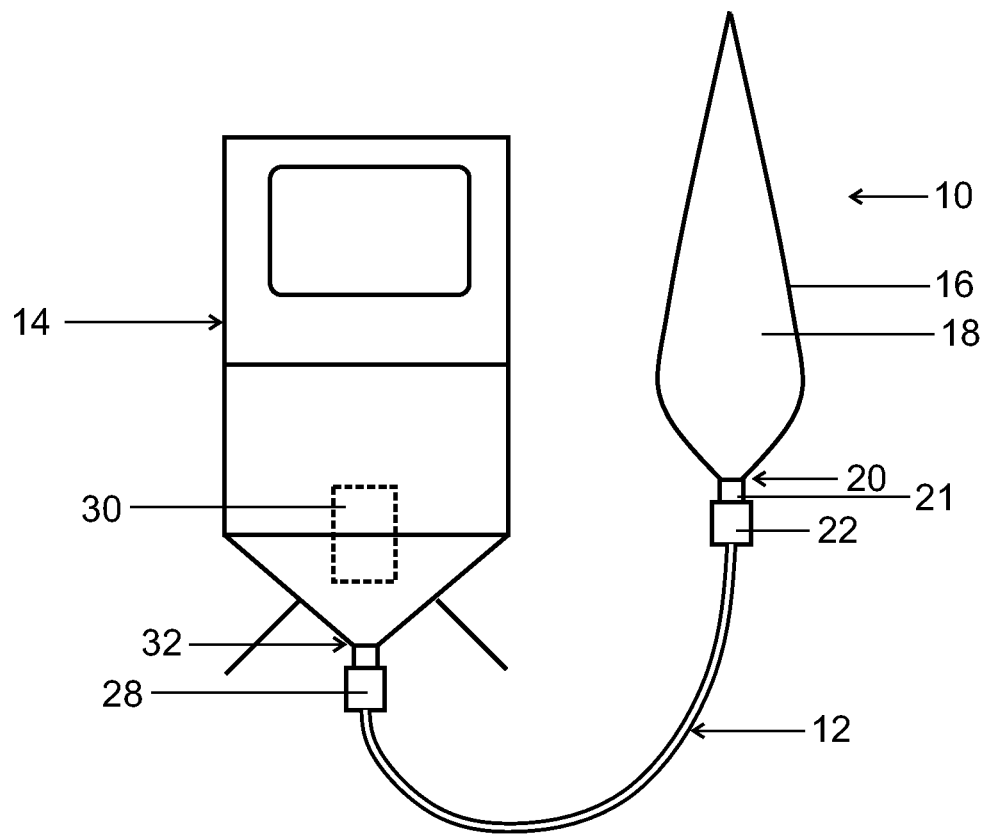
FIG. 1 is a schematic view of a calibration suspension unit according to the present invention comprising a hose line system that is connected to a turbidity meter.

FIG. 1 shows a calibration suspension unit according to the present invention 10 that is connected to a turbidity meter 14 via a hose line system 12. The calibration suspension unit 10 comprises a flexible container 16, for example a foil bag, that is filled with a calibration suspension 18 for turbidity measurement and has at least one opening 20, for example in the form of a plastic sleeve 21 attached to the bag that is sealed by a septum lid 22.

The container 16 is made of a flexible material, in particular of a plastic film, a metal foil or a composite film that may be formed by several layers of plastic films and/or metal foils.

The hose line system 12 comprises a hose line 24 with a first free end at which a cannula 26 (FIG. 5) is provided. At the opposite free end of the hose line 24 a connection 28 (FIGS. 6a and 6b) is provided suitable for connecting the hose line 24 to the turbidity meter 14.

The turbidity meter 14 has a measuring body 30, in particular a flow measuring body that is provided for determining the turbidity values of the samples introduced into the measuring body and can both be filled and emptied via an outlet valve.

Figure 2A:
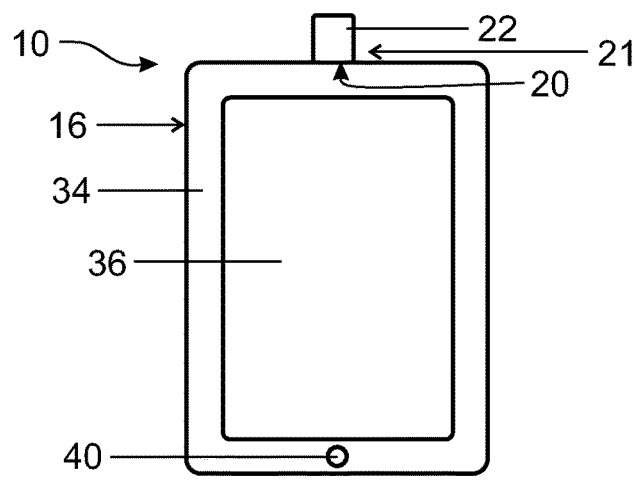
FIGS. 2a, 2b and 2c are schematic views of embodiments of the flexible container of a calibration suspension unit according to the present invention.
Figure 2B:
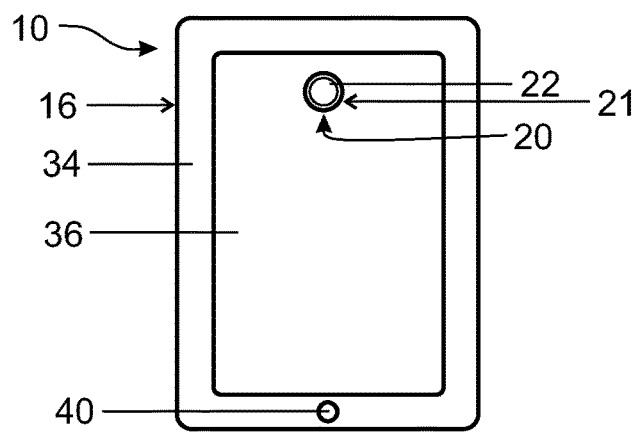
Figure 2C:
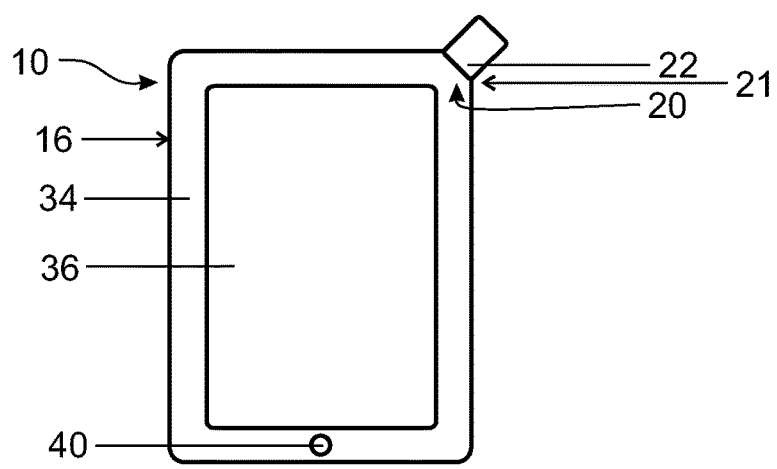

In FIGS. 2a, 2b and 2c various embodiments of the calibration suspension unit 10 are shown whose container 16 is designed as a rectangular, cushion-shaped foil bag. The container 16 consists of two plastic films lying one above the other that are closely connected to each other in a circumferential fringe area 34, for example by welding, gluing or hot-sealing, and form an interior 36 provided for receiving the calibration suspension 18.

Alternatively, the container 16 can be designed as a balloon, a stand-up pouch or a tubular bag and, accordingly, exhibit a smaller or no fringe area 34. The tubular bag can be made of a flat film or a film tube, with or without a fringe area, and have an opening 20 in the form of a plastic sleeve 21 incorporated into the bag. In FIG. 2a, the plastic sleeve 21 is incorporated centrally in a head seam of the container 16, in FIG. 2b the plastic sleeve 21 is incorporated into the interior 36 and in FIG. 2c the plastic sleeve 21 is incorporated into a head seam at a corner of the container 16. Stand-up pouches usually have a bottom area designed as a W fold.

The opening 20 formed by the plastic sleeve 21 can be integrally formed to the container 16 or firmly bonded with it, in particular glued or welded. The opening 20 is closed by the septum lid 22. Preferably, the opening 20 has a thread 38, preferably an external thread (see FIG. 3), to which the septum lid 22 provided with an internal thread can be attached as a screw cap. Alternatively, the septum lid 22 can be clamped onto the opening 20.

At the end opposite to the opening 20 the container 16 has an eyelet 40 from which the calibration suspension unit 10 may be suspended and/or which can be used for labeling the calibration suspension unit 10.

The container 16 is not completely filled with the calibration suspension 18. This means that the maximum volume of the container 16 is larger than the volume of the calibration suspension 18 introduced into the container 16. The ratio of the volume of the calibration suspension 18 to the maximum volume of the container 16 may be from 0.2 to 0.8, preferably from 0.4 to 0.6.

However, the calibration suspension unit 10 is substantially free of air, i.e. the container 16 is only filled with the air bubble-free calibration suspension 18 and there is no air supernatant or dead volume. A formazine suspension is preferably used as a calibration suspension 18.

A calibration suspension unit 10 according to the present invention can contain up to 1,500 ml calibration suspension 18. Preferably, the calibration suspension unit 10 is filled with 100 ml to 1,200 ml calibration suspension 18.

In addition, the calibration suspension unit 10 preferably contains a larger volume of the calibration suspension 18 than the volume of the flowmeter 30 to be filled.

Figure 3:
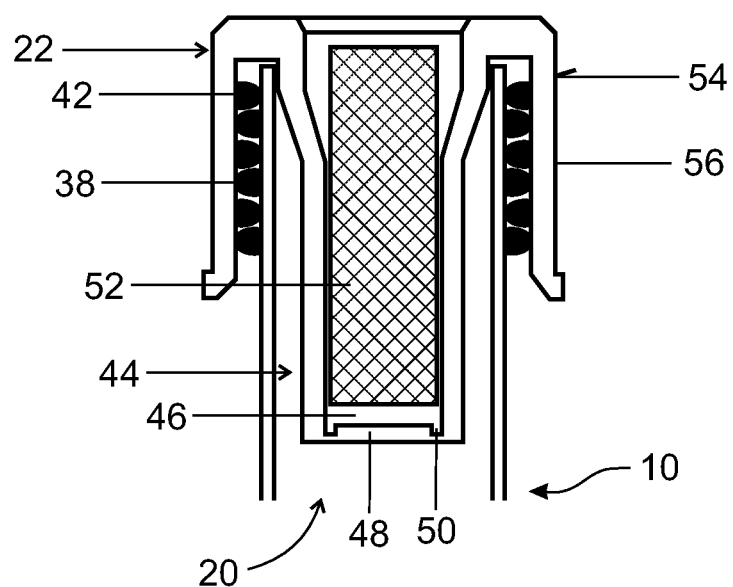
FIG. 3 is a sectional view of a septum lid of a calibration suspension unit according to the present invention.

In FIG. 3, a section of a calibration suspension unit 10 according to the present invention with a septum lid 22 made of plastic is shown in a sectional view. The septum lid 22 has an internal thread 42 that is screwed onto the external thread 38 of the opening 20 for the septum lid 22 to tightly close the opening 20 of the container 16.

The septum lid 22 comprises a cylinder-shaped extension 44 protruding into the opening 20 and intended to displace the calibration suspension 18 (not shown) present in the opening 20 when placing the septum lid onto it. As the extension 44 is distanced from the inner circumference of the opening 20, the calibration suspension displaced by the extension 44 can overflow from the opening 20. The overflowing calibration suspension 10, in turn, displaces the air still enclosed in the opening to obtain a closed calibration suspension unit 10 without any air inclusions.

The extension 44 has an axial channel 46 that is closed by a final section 48 at its axial end facing the container 16. The final section 48 has a groove 50 circulating along the inner circumference of the channel 46 at the inner surface of the cylinder-shaped extension 44 that acts as a predetermined breaking point if a cannula 26 (see FIG. 4) for tapping the calibration suspension unit 10 is introduced into the channel 46 of the septum lid 22. The diameter of the channel 46 is preferably larger than the external diameter of the cannula 26.

A sealing element 52 inserted into the channel 46 is placed in the cylinder-shaped recess 44 completely filling and sealing the extension 44 in the radial direction. The sealing element 52 acts as a sealing reception for a penetrating cannula 26 whose external diameter is smaller than the diameter of the channel 46.

In addition or alternatively, the end of the channel 46 facing outwards can be closed with a protective film or a sealing membrane (not shown).

The septum lid 22 has a surface 56 that is corrugated in an axial direction at its outer shell surface 54 provided for easier handling of the septum lid 22.

Figure 4A:
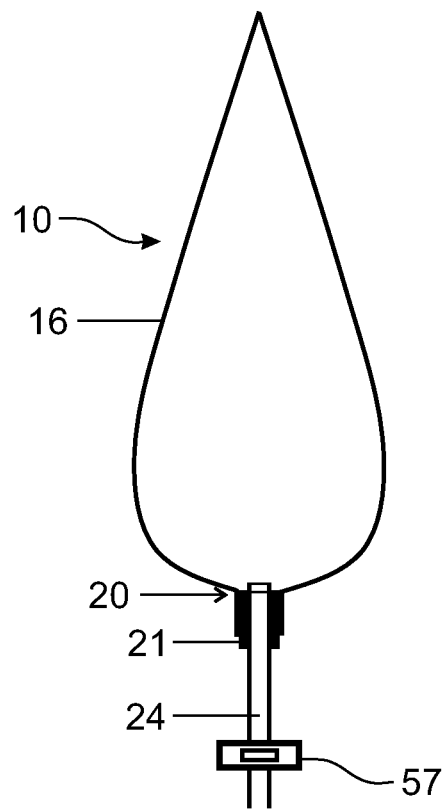
FIGS. 4a and 4b are sectional views of embodiments of a calibration suspension unit according to the present invention comprising a hose line system.

In FIG. 4a an alternative embodiment of the calibration suspension unit 10 with a hose line system 12 directly connected to the flexible container 16 is shown, with the container 16 being tightly linked with the hose line 24. In the embodiment shown here the hose line 24 is welded to the plastic sleeve 21 incorporated into the opening 20 in the flexible container 16.

In an alternative embodiment (not shown) a lid can be provided at the opening 20 that is directly connected to the hose line 24 or has an connection for the hose line 24 that is open towards the flexible container 16.

In all these cases the flexible container 16 is tightly closed by disconnecting the hose line 24 by means of a hose clamp 57. The hose clamp 57 is preferably arranged at the hose line 24 close to the opening 20 of the flexible container 16. As the calibration suspension 18 in the flexible container 16 forms a supernatant in the hose line 24, there exists no air supernatant or dead volume in the flexible container 16.

Figure 4B:
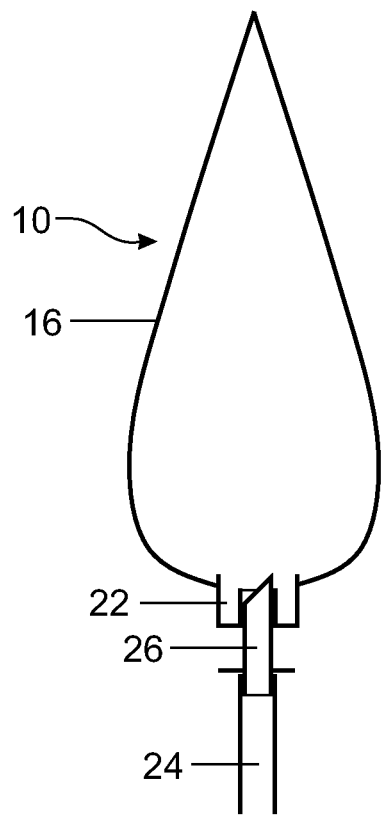

In FIG. 4b a calibration suspension unit 10 with a septum lid 22 pursuant to FIG. 3 is shown that is tapped by means of a cannula 26 attached to the hose line 24. In this embodiment, the hose line 24 with the cannula 26 is provided as a separate hose line system 12.

To use the calibration suspension unit 10 for the calibration of a turbidity meter 14 the calibration suspension 18 is mixed homogeneously and introduced into the turbidity meter 14 without any air bubbles being formed.

To this end, the flexible container 16 of the calibration suspension unit 10 is mechanically deformed shortly before use; for example, the flexible container 16 is manually kneaded and/or shaken by the user. To obtain a homogeneous calibration suspension 18 kneading for a period of about 10 seconds to 2 minutes, preferably of up to 1 minute, particularly preferably from 15 to 30 seconds is sufficient. According to the present invention "shortly before use" means a period of up to 10 minutes. If the calibration suspension unit 10 is not used during this period, renewed mixing of the suspension by kneading or shaking is recommended.

Figure 5:
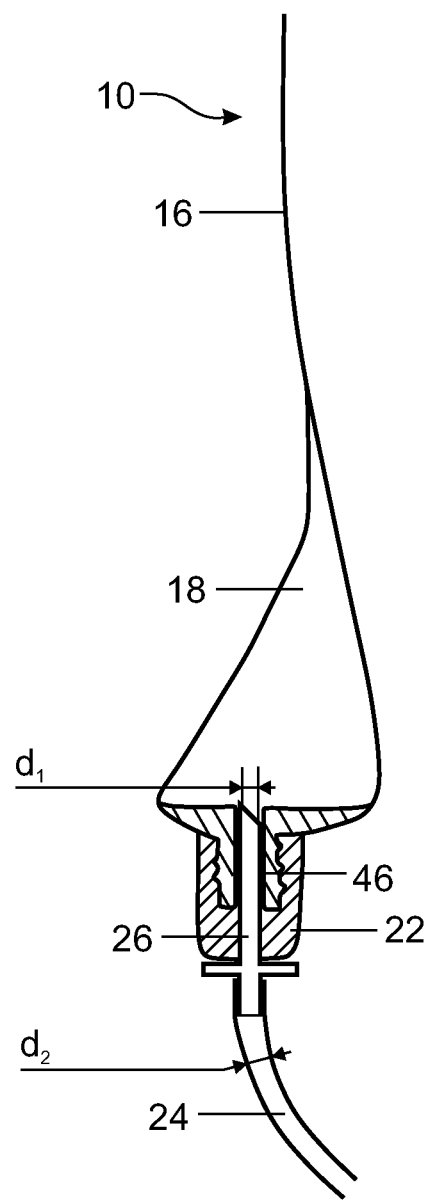
FIG. 5 is a sectional view of another embodiment of a calibration suspension unit according to the present invention comprising a hose line system.

To fill the turbidity meter 14 without any air bubbles being formed, the calibration suspension unit 10 is tapped as shown in FIG. 5. To this end, the calibration suspension unit 10 is suspended with the opening 20 facing downwards, i.e. in the direction of the ground. The channel 46 placed in the septum lid 22 is then punctured by the cannula 26 arranged at the hose line 24, thus connecting the hose line 24 to the calibration suspension unit 10 and the calibration suspension 18 contained in the container 16. As the hose line 24 is closed during this connection, for example by a stop valve 58 (FIG. 6a) or by disconnection using a clamp 62 (FIG. 6b), no air can penetrate into the calibration suspension 18. Subsequently, the hose line 24 is connected to the turbidity meter 14 and the hose line 24 is opened. Alternatively, the hose line 14 can first be connected to the turbidity meter 14 and then the septum lid 22 can be punctured by the cannula 26. In this case, the hose line 24 does not have to be closed prior to its connection to the turbidity meter 14.

When using a calibration suspension unit 10 with a hose line system 12 directly connected to the flexible container 16 (FIG. 4a), a closure optionally arranged at the free end of the hose line 24 can be opened and the hose line 24 can be connected to the turbidity meter 14. As the hose line 24 is still closed by the clamp 57, no air can penetrate into the calibration suspension. After connecting the hose line 24 to the turbidity meter 14 the calibration suspension unit 10 is suspended with the opening 20 facing downwards and the clamp 57 is removed allowing the calibration suspension 18 to flow into the turbidity meter 14 without any air bubbles being formed.

The internal diameter $d_1$ of the cannula 26, if present, and the internal diameter $d_2$ of the hose line 24 are selected such that the calibration suspension 18 displaces the air from the calibration suspension unit 10 towards the turbidity meter 14 without any air bubbles rising through the hose line 24 into the container 16. Simultaneously, the internal diameters $d_1$, $d_2$ are calculated such that the measuring body 30 in the turbidity meter is filled at sufficient speed.

To this end, an internal diameter $d_1$, $d_2$ of the cannula 26 and/or the hose line 24 of less than 9 mm, in particular from 3 to 7 mm, is particularly suitable. The filling time depends on the volume of the measuring body 30. Filling a measuring body 30 with a volume of 300 ml takes from 40 to 60 seconds.

Figure 6A:
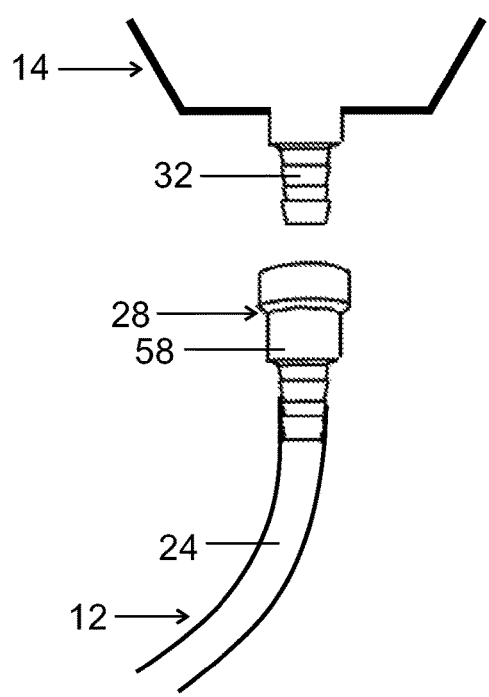
FIGS. 6a and 6b are schematic views of the connection of a turbidity meter to the hose line system of a calibration suspension unit according to the present invention.
Figure 6B:
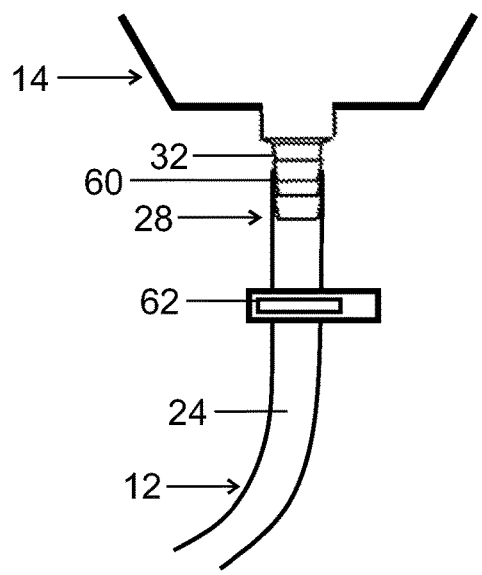

In FIGS. 6a and 6b two different embodiments of the present invention are shown illustrating how the hose line system 12 is connected to the turbidity meter 14.

The outlet valve 32 of the turbidity meter 14 is provided to drain samples from the measuring body 30 for calibration and verification purposes. According to the present invention, the outlet valve 32 is used to fill the calibration suspension 18 into the measuring body 30 without any air bubbles being formed. To this end, the calibration suspension unit 10 is connected to the outlet valve 32 via the hose line system 12.

In the embodiment shown in FIG. 6a the hose line system 12 has a stop valve 58 at its connection 28 that can be connected to the outlet valve 32. The stop valve 58 is closed when not connected and opens spontaneously when placed on the outlet valve 32.

Alternatively, as shown in FIG. 6b, the connection 28 of the hose line system 12 can be designed as a free line end 60 of the hose line 24. In this case, an undesired flow of the calibration suspension 18 is prevented by disconnecting the hose line 24, for example, by means of a clamp 62. To connect the hose line system 12 to the turbidity meter 14 the free line end 60 is pushed over the outlet valve 32 and secured by a clip (not shown), if required.

After homogenous mixing of the calibration suspension 18, tapping of the calibration suspension unit 10 and, as shown in FIG. 1, connecting it to the turbidity meter 14 via the hose line system 12, the measuring body 30 can be filled.

To fill the measuring body 30 the calibration suspension unit 10 is arranged with the opening 20 facing downwards at a greater geodetical height than the measuring body 30, for example by suspending the calibration suspension unit 10 from the eyelet 40 (see FIG. 2). If the hose line 24 is blocked by a clamp 57 and/or 62, this clamp is removed thus opening the connection. Due to the hydrostatic pressure the calibration suspension 18 flows out of the container 16 into the measuring body 30 possibly filling it completely. The container 16 contracts without generating a vacuum that would draw in air.

As neither during mixing of the calibration suspension 18 in the air-free container 16 nor during filling of the measuring body 30 via the hose line system 12, in which process the calibration suspension 18 displaces all of the air, any air bubbles are enclosed in the calibration suspension 18, it is possible to fill the turbidity meter 14 with the calibration suspension 18 without any air bubbles being formed.

After measurement of the calibration suspension 18 has been finished, the empty calibration suspension unit 10 connected to the device is brought to a lower geodetical height than the flow measuring body 30, thus making the calibration suspension 18 flow back into the container 16. If the opening 20 of the container 16 is held upside down during this process, no air can flow back into the container 16. After the entire calibration suspension 18 has flown back, the hose line 24 is again closed and disconnected from the turbidity meter 14.

Thus, the calibration suspension unit 10 can be used several times, if required. Optionally, if the calibration suspension unit 10 cannot be re-used, it can be professionally disposed of together with the hose line system 12.

Due to the provision of the calibration suspension 18 in the calibration suspension unit 10 of the present invention the user saves much time and can perform a correct measurement. Simultaneously, safe handling of the calibration suspension 18 is ensured as neither the user nor the environment comes into direct contact with the calibration suspension 18.

For the manufacture of the calibration suspension unit 10 of the present invention a method comprising the following steps is provided:

In a first step the container 16 is filled with the calibration suspension 18. The volume of the calibration suspension 18 that is filled into the container 16 is preferably slightly larger than the volume of the calibration suspension 18 that is to be present in the final calibration suspension unit 10.

In a second step the air present above the calibration suspension in the container 16 is completely removed. The air can be removed from the container 16 by mechanically compressing the flexible container 16.

In a third step the container 16 will be closed without any air supernatant being present. To this end, it is preferred to use a septum lid 22, or a hose line directly connected to the flexible container 16 is disconnected at a section filled with the calibration suspension 18.

Figure 7A:
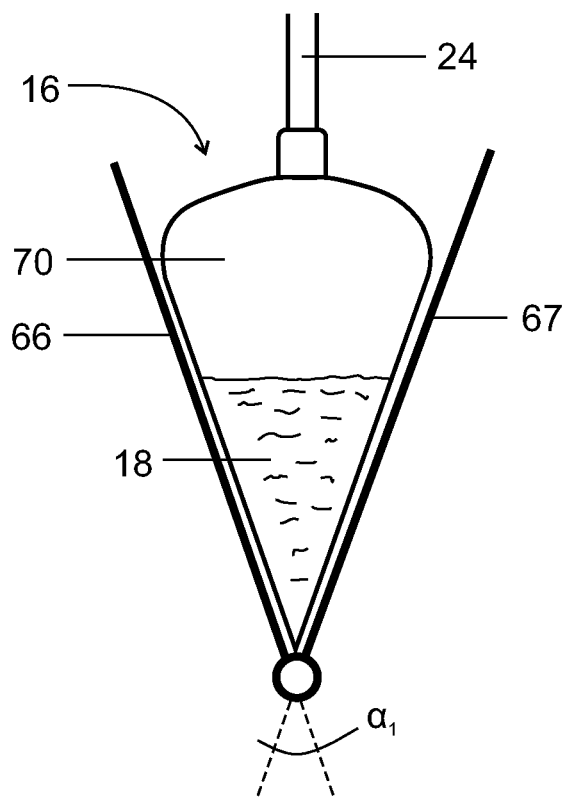
FIGS. 7a and 7b are schematic views of a method according to the present invention for the filling of a calibration suspension unit according to the present invention.
Figure 7B:
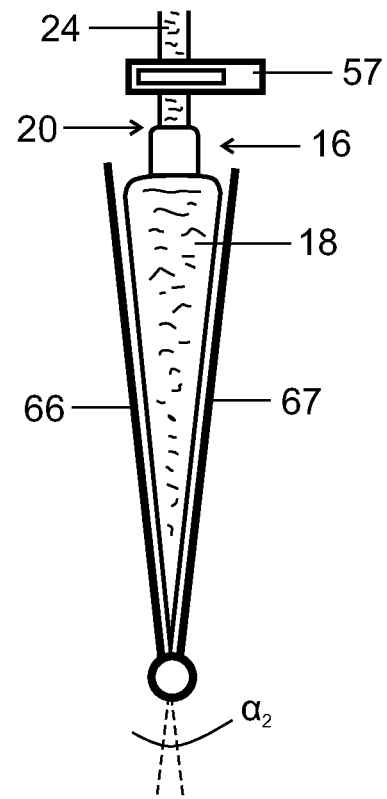

In FIGS. 7a and 7b a method for filling the container 16 with the calibration suspension 18 and for removing air from the container 16 is shown. The container 16 is positioned between two panels 66, 67 arranged in a V shape (see FIG. 7a) and, at this point of time, can already be partially compressed by the two panels 66, 67. The volume enclosed by the two panels 66, 67 is smaller than the maximum volume of the container 16. Subsequently, the container 16 is filled with the calibration suspension 18 (see FIG. 7b). While being filled the container 16 can expand only up to the plates 66, 67. Preferably, the container 16 is filled such that the calibration suspension 18, when reaching the desired filling volume, overflows at the opening 20 of the container 16 and is pressed into the hose line 24 directly connected to the flexible container 16. Then, the hose line 24 can be disconnected at a section filled with the calibration suspension 18 by means of a clamp 57, and the calibration suspension unit 10 can thus be closed without any air bubbles being formed.

The desired filling volume of the calibration suspension 18 can be determined by the angle $\alpha_1$, $\alpha_2$ between the two panels 66, 67. The panels 66, 67 can also be mounted to be movable against each other to make it possible for the container 16 to be filled and the calibration suspension 18 to be made to overflow by a movement of the panels 66, 67 with respect to each other. Thus, the entire air 70 is displaced from the container 16 and the container 16 can be subsequently closed by using a septum lid 22 or by disconnecting the hose line 24 at a section filled with the calibration suspension 18 by means of a clamp 57 without any air bubbles being formed.

Figure 8A:
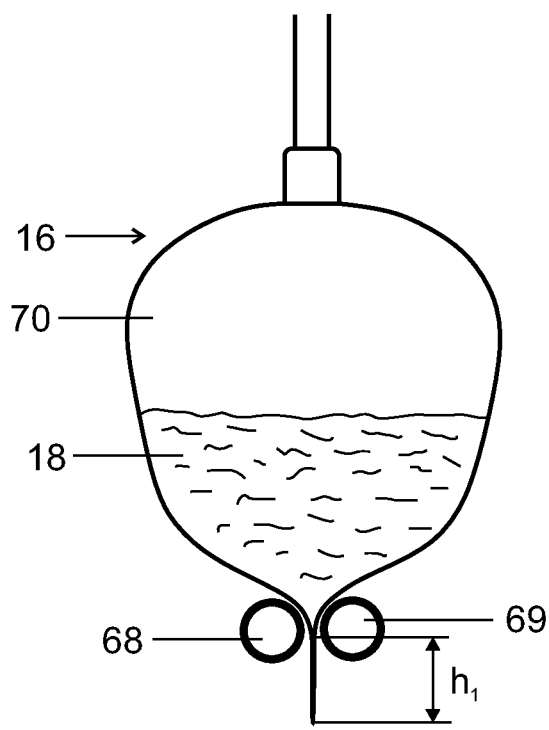
FIGS. 8a and 8b are schematic views of another method according to the present invention for the filling of a calibration suspension unit according to the present invention.
Figure 8B:
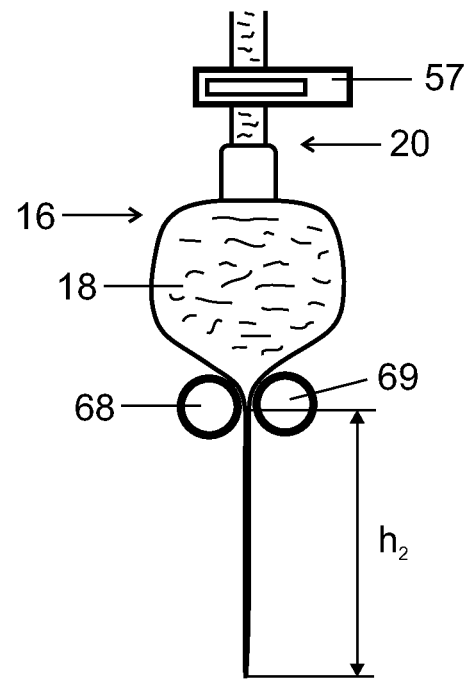

In FIGS. 8a and 8b another method for filling the container 16 with the calibration suspension 18 and for removing air 70 from the container 16 is shown. Instead of the V-shaped panels 66, 67 the container 16 is compressed up to a certain height $h_1$, $h_2$, for example by rolls 68, 69, and disconnected there (see FIG. 8a). Now the part above the rolls 68, 69 that is not compressed is filled with the calibration suspension 18. While being filled the container 16 can only expand up to the rolls 68, 69, which makes the container 16 run over at its opening 20 when reaching the desired filling volume of the calibration suspension 18. The desired filling volume of the calibration suspension 18 can be determined by the height $h_1$, $h_2$ of the area compressed by the rolls 68, 69. Alternatively, for filling up to the overflow, the partially filled container 16 can be further compressed by the rolls 68, 69 thus reducing the filling volume of the container 16 up to the overflow. Thus, all of the air 70 is displaced from the container 16 and the container 16 can subsequently be closed by using a septum lid 22 or by disconnecting the hose line 24 by means of the clamp 57 without any air supernatant being present.

For the airless closure of the container 16 the septum lid 22 shown in FIG. 3 can be used. When the septum lid is placed onto the container 16 filled to the brim and screwed down, the extension 44 displaces the calibration suspension 18 and air 70 that might still be present from the area of the opening 20, thus closing the container 16 without any air bubbles being formed, i.e. without air 70 being enclosed in the container 16.

If the hose line 24 is directly connected to the flexible container 16, the container 16 is compressed until no air 70 is left in the container and in a part of the hose line 24. Then, the hose line 24 is disconnected at a location filled with the calibration suspension 18, preferably close to the container 16, by means of a clamp 57; as a result no air 70 is enclosed in the container 16 and in the part of the hose line 24 disconnected accordingly.

The calibration suspension unit 10 manufactured this way can then be used for the calibration of a turbidity meter 14, as described above.

The invention claimed is:

1. A calibration suspension unit comprising a container that is filled with a calibration suspension for the calibration of a turbidity meter, wherein the calibration suspension is a suspension of particles selected from the group consisting of formazine, styrene divinyl benzene, latex or metal oxide gel in a liquid, and wherein the container is made of a flexible material, and wherein there exists no air supernatant above the calibration suspension in the container.

2. The calibration suspension unit according to claim 1, wherein the container is a foil bag.

3. The calibration suspension unit according to claim 1, wherein the container has a wall having a thickness of less than 1 mm.

4. The calibration suspension unit according to claim 1, wherein the container is air-tight and impermeable to liquids.

5. The calibration suspension unit according to claim 1, wherein the container is impermeable to light.

6. The calibration suspension unit according to claim 1, wherein the container is made of at least one of a plastic film and a metal foil.

7. The calibration suspension unit according to claim 1, wherein a maximum volume of the container is larger than a volume of the calibration suspension in the container.

8. The calibration suspension unit according to claim 1, wherein the calibration suspension unit comprises a hose line system, the hose line system comprising a hose line directly connected to the flexible container.

9. The calibration suspension unit according to claim 1, wherein the calibration suspension unit comprises a hose line system, the hose line system comprising a hose line and a cannula provided at the hose line.

10. The calibration suspension unit according to claim 9, wherein the container is closed by a septum lid.

11. The calibration suspension unit according to claim 8, wherein the hose line has an internal diameter d2 and optionally the cannula has an internal diameter d1 of 9 mm at the most, preferably from 3 to 7 mm.

12. A method for manufacturing of a calibration suspension unit according to claim 1, comprising the steps of:
  a) providing a container made of a flexible material and a calibration suspension wherein the calibration suspension is a suspension of particles selected from the group consisting of formazine, styrene divinyl benzene, latex or metal oxide gel in a liquid;
  b) filling the calibration suspension into the container,
  c) removing substantially all air from the container, and
  d) closing the container,
  wherein there is no air supernatant above the calibration suspension in the closed container.

13. The method according to claim 12, wherein the air is removed by mechanical compression of the container.

14. A method of calibrating a turbidity meter using a calibration suspension unit according to claim 1, wherein the calibration suspension is introduced into the turbidity meter without substantial air bubble formation.

15. The method according to claim 14, wherein the calibration suspension is mixed by mechanical deformation of the calibration suspension unit.

16. The method of claim 14, wherein the calibration suspension is introduced into the turbidity meter by means of a hose line, wherein the flexible container collapses as the calibration suspension escapes from the container without air being drawn in as a volume compensation for the calibration suspension, and wherein all air in the hose line is displaced by the calibration suspension without forming of any air bubbles in the calibration suspension.

17. The calibration suspension unit of claim 7, wherein a ratio of the volume of the calibration suspension to the maximum volume of the container is from 0.2 to 0.8.

18. The calibration suspension unit of claim 8, wherein the hose line is detachably connected to the flexible container.

* * * * *